United States Patent [19]

Lui

[11] Patent Number: 4,944,945

[45] Date of Patent: Jul. 31, 1990

[54] PHARMACEUTICAL COMPOSITION FOR INHIBITING VIRUSES AND INCREASING IMMUNE FUNCTION (PII)

[76] Inventor: Yaguang Lui, 67-08 168th St., Flushing, N.Y. 11365

[21] Appl. No.: 396,332

[22] Filed: Aug. 21, 1989

Related U.S. Application Data

[62] Division of Ser. No. 6,736, Jan. 27, 1987, Pat. No. 4,886,666.

[51] Int. Cl.$^5$ ............................................. A61K 35/78
[52] U.S. Cl. .................................................. 424/195.1
[58] Field of Search ...................................... 424/195.1

[56] References Cited

PUBLICATIONS

Chem. Abst. 102:100671n, 1985.
Chem. Abst. 102:119483z, 1985.
Chem. Abst. 106:162663z, 1987.

Primary Examiner—John W. Rollins
Attorney, Agent, or Firm—Chenpatents

[57] ABSTRACT

A safe pharmaceutical composition for treatment and prevention of infections caused by viruses and increasing immune function. The pharmaceutical composition is composed of four active ingredients: Polysaccharides of Wang Qi, Banlankensu, Yejuhua-flavonoid and Guanzhongsu and method of making the same.

1 Claim, No Drawings

PHARMACEUTICAL COMPOSITION FOR INHIBITING VIRUSES AND INCREASING IMMUNE FUNCTION (PII)

This application is a division, of application Ser. No. 07/006,736, filed Jan. 27, 1987, now U.S. Pat. No. 4,886,666.

BACKGROUND OF THE INVENTION

The present invention related to novel pharmaceutical composition for treatment and prevention of infections caused by viruses and increase immune function, processes for the production of these pharmaceutical composition and the use thereof. The bifunctional pharmaceutical composition is nontoxic.

Specifically, this invention provides a new safe pharmaceutical composition of four active ingredients:
(1) Polysaccharide of Wang Qi is extracted from *Astragalus membranaceus* Bge or other species of Astragalus;
(2) Banlankensu is extracted from among *Isatis tinctoria* L, *I. indigotica* Fort or *Baphicacanthus cusia* Bremek;
(3) Yejuhua-flavonoid is extracted from *Chrysanthemum indicum* L;
(4) Guanzhonhsu is extracted from among *Dryopteris crassirhizoma* Nakai, *Osmunda japonica* Thunb, *Lunathyrium acrostichoides* Ching or *Matteuccia stuthiopteris* Todaro.

For the sake of convenience, composition comprising mixtures of the above extracts will hereinafter be referred to as "PII".
P: Pharmaceutical Composition:
I: Inhibiting virus;
I: Increasing Immune Function.

DESCRIPTION OF THE PRIOR ART

The major antiviral drugs can inhibit viral replication but also inhibit some host cell function and possess serious toxicity. For example, amantadine, idoxuridine, cytarabine, vidarabine are major antiviral drugs using in clinic now. Amantadine can inhibit myxoviruses, e.g, influenza A, rubella. The most marked toxic effects of amantadine are insomnia, slurred speech, dizziness, ataxia and other central nervous system sign. Idoxuridine can inhibit the replication of herpes simplex virus in the cornea, however DNA synthesis of host cells is also inhibited. Cytarabine can inhibit DNA synthesis and interferes with replication of DNA viruses. But cytarabine also inhibit immune function in human. By weight it is about 10 times more effective than idoxuridine, and it is also 10 times more toxic for host cell. Vidarabine can inhibit herpesvirus, but it is also produce more marked adverse gastrointestinal or neurologic side-effects.

As mentioned above, so far there obviously still lacks any effective antiviral drug and at the same time there is nothing to do with the side effect.

On the other side, *Isatis tinctoria* L., *I. indigotica* Fort, *Baphicacanthus cusia* Bremek, *Chrysanthemum indicum* L, *Dryopteris crassirhizoma* Nakai and *Osmunda japonica* Thunb as natural herbs used in clinic for treatment and prevention of infections caused by some viruses such as hepatitis B virus, influenzavirus, bronchitisvirus, mumpsvirus et al.

Reference:
(1) Liaoning Medicine 1:5 1974;
(2) New Medicine 4:219 1975;
(3) Hunan Science and Technical Information 15:47 1972.

Although all of the above Natural herbs have been individually utilized in traditional chinese herb for a variety of treatments. It has not been previously disclosed that the four active components in combination would produce a composition with the remarkable synergistic therapeutic effects of the compositions of the present invention.

DETAILED DESCRIPTION

Viruses are obligate intracellular parasites. Their replication depends on metabolic processes of the host cell. Therefore major antiviral drugs that inhibit viral replication also inhibit some host cell function and possess serious toxicity. Although some vaccines developed already, but many viral diseases are caused by different viruses. For example, the common cold is caused by a great variety of different viruses. That is why the same person may have so many different attacks, and why the symptoms may be a bit different from one attack to another.

So much more, the immune function normally protects human being from infections caused by viruses. The results of research indicated that viral infection tends to cause disease only in individual whose immune function has been severely weakened. Individual with health immune function could control virus without the serious effects that occur with the disease.

For reason given above, a new pharmaceutical composition which has bifunction—inhibit viruses and increase immune function—is very important for treatment and prevention of infections caused by virus. PII just has above bifunction.

In short, PII can inhibit viruses and increase immune function and it is safety.

The following specific examples will provide detailed illustrations of methods of prodicing PII according to the present invention and pharmaceutical dosage units containing PII. Moreover, examples will be given of pharmaceutical testing performed with PII which demonstrates its effectiveness in inhibiting viruses and increasing immune function. These examples are not intended, however, to limit or restrict the scope of the invention in any way, and should not be construed as providing conditions, paratemters, reagents, or starting materials which must be utilized exclusively in order to practive the present invention.

EXAMPLE 1

Extraction of Polysaccharide of Wang Qi 2,000 ml of water was added to 1,000 g of dry powder *Astragalus membranaceus* or other species of Astralus. The solution was heated to boil and simmered one-half hours after boiling. This water extraction was repeated once and the two extracts combined and filtered. The filtrate was concentrated under reduced pressure to approximately 500 ml and 95% ethanol was added to the concentrate to a final ethanol concentration of 60%. The solution was filtered and the precipitate dissolved in an appropriate amount of water, filter to remove the residue and filtrate saved. The filtrate was concentrated under reduced pressure to 200 ml and 95% ethanol added to the concentrated to a final ethanol concentration of 80%. The solution was allowed to stand at 4° C. overnight. The supernatant was then discard and the precipitate washed three times with 95% ethanol and then twice with acetone and ether consecutively. The product was vacuum dried.

EXAMPLE 2

Extraction of Banlankensu

The roots of *Isatis tinctoria* L, or *I. indigotica* Ford were dried and powdered.

3 liters of 95% ethanol was added to 1 kg powders of roots and allowed to stand for one day at room temperature. The solution was filtered and the extract filtrate save. 2,000 ml of ethanol was added to the residue and refluxed in a water bath for 6 hours. The refluxing was repeated twice by collecting the ethanol, replacing it with an equal volume of fresh 95% ethanol and refluxing for 6 hours. The refluxed ethanol was cooled and filtered and the filtrate combined with the extract filtrate. Ethanol was then recovered by reduced pressure distillation and the residue dissolved in 500 ml of distilled water. The lipid component was removed with 5 changes of ether by adding 500 ml to the water phase for each extraction. An equal volume of water-saturated butanol was added to the final water phase and the butanol was then distilled under reduced pressure. The residue powder was dissolved in 500 ml of ethanol and 2,000 ml of acetone was added to the ethanol with constant stirring while a precipitate formed. The precipitate was washed twice each with acetone and ether and dried.

EXAMPLE 3

Extracted Yejuhua-flavonoid

Plants or flowers of *Chrysanthemum indicum* L were dried and powdered. 1 kg of the powder was dipped in 2 liters of 95% ethanol for about 24 hours at room temperature. The solution was filtered and the extract filtrate save. 2 liters of 95% ethanol was added to residue and refluxed in water bath and refluxing for 6 hours. The refluxed ethanol was cooled and filtered and the filtrate combined with the extract filtrate. Ethanol was then recovered by reduced pressure distillation to remove the ethanol. Residue saved. 1000 ml of aceticether was added to residue and refluxed in a water bath for 6 hours. The refluxing procedure was repeated. Aceticether was then concentrated under reduced pressure distillation. Crystals were formed. Crystals were washed with water. Final crystals were dried under vacuum and was found to have a melting point of about 250° C.

EXAMPLE 4

Extraction of Guanzhongsu

The roots and stems of *Dryopteris crassirhizoma* Nakai or *Osmunda japonica* Thunb were dried and powdered.

10 liters of water was added to 1 kg of dried powders. The solution was heated to boil and simmered one-half hours after boiling. This extraction was repeated once and the two extracta combined and filtered. The filtrate was concentrated to 5 liters and then concentrated under reduced pressure to approximately 500 ml. 95% of ethanol was added to the concentrate to a final ethanol concentration of 75%. The solution of 75% ethanol was filtered the residue (A) and filtrate saved. The filtrate was concentrated under reduced pressure to 150 ml. 100 ml of water was added to 150 ml of concentrated filtrate then concentrated under reduced pressure to 150 ml and allowed to stand at 4° C. The solid precipitate (A) was separate then filtered with vacuum filter and filtrate (A) saved. Residue (A) was extracted with 1N sodium hydroxide. Filtered and filtrate (B) were saved. Sodium hydroxide was added to filtrate (A) to a final sodium hydroxide concentration of 1N and combined with filtrate (B) then neutralized with 1N of HCl. Neutralized solution allowed to stand at 4° C. Solid precipitate (B) was separate and combined with solid preciptate (A). Solid precipitate was dried under vacuum and powdered.

EXAMPLE 5

Preparation of fine product of PII

Fine PII preparation according to the present invention consists of:

|  | Weight Percent | Preferred weight percent |
| --- | --- | --- |
| Polysaccharide of Wang Qi | 40–95% | 85% |
| Banlankensd | 1–30% | 5% |
| Yejuhua-flavonoid | 1–30% | 5% |
| Guanzhongsu | 1–30% | 5% |

EXAMPLE 6

Preparation of curde product of PII

Crude PII is extracted from as mentioned above plants by ethanol and water. Proportion of plants, for example, is as following (by weight):

|  | Weight percent | Preferred Weight percent |
| --- | --- | --- |
| *Astragalus membranaceus* Bge or other species of *Astragalus* | 10–70% | 55% |
| *Isatis tinctoria* L or *I, indigotica* Fort | 5–50% | 15% |
| *Chrysanthemum indicum* L. | 5–50% | 15% |
| *Dryopteris crassirhizoma* Nakai or *Osmunda japonica* Thunb | 5–50% | 15% |

Tissue of plant were dried and powdered. 5 liters distallatory water was added 1 kg of dried powder. The solution was heated to boil and simmered for one hour after boiling. This water extraction was repeated two times. Combined and filtered. The filtrate was concentrated under reduced pressure to approximately 500 ml. Then 1000 ml 95% ethanol was added to 500 ml water solution. Stir. Stilled. Filtered. Residue and filtrat (A) was obtained. 1000 ml 90% ethanol was added to residue. Stir. Extraction of 90% ethanol was combined. Filtered. Filtrate (B) was obtained. Combined filtrate (A) with (B). Then total filtrate was concentrated to syrup under reduced pressure distillation. Ethanol was recoved. Syrup dried under vacuum drying. Granulated to final powder. Weight of every capsule and table is about 200–500 mg. Crude-PII is similar to fine-PII in pharmacological property.

EXAMPLE 7

In vitro antivirus activity

The cell system consiste of monolayers of a continuous human cell line, the HeLa cell, infected with RNA virus and DNA virus. From RNA virus, the representatives of Rhabdoviridae Picornaviridae, Adenoviridae, Reoviridae and Paramyxoviridae were inhibited obviously. From DNA viruses, the representatives of Adenoviridae, Herpesviridae (HSV) and Poxviridae were inhibited obviously too. As results of Table 2 indicate that PII has good broad spectrum antiviral activity against both DNA and RNA viruses. HeLa cells were grown in monolayer culture in following medium:

TABLE 1

| A. | | mg/liter | mM |
|---|---|---|---|
| | NaCl | 6800 | 117.2 |
| | KCl | 400 | 5.4 |
| | $MgSO_2\ 7H_2O$ | | |
| | $NaH_2PO_4\ H_2O$ | 1400 | 10.0 |
| | $NaHCO_3$ | 2000 | 23.8 |
| | Glucose | 1000 | 5.6 |
| | Phenol red | 10 | |
| B. | Whole human serum: | | 10% (W/W) |

The monolayers of HeLa cell were prepared and cultivated. Culture flasks were used for experiments 72 to 96 hours after planting at which time cell counts had reached 2.5 to $3.0 \times 10^6$ per flask. The cells in monolayer culture were washed with solution of virus. After infection the flasks were incubated at 37° C. The sample of the supernatant fluid at the conclusion of the adsorption period were titrated to determine the number of plaque-forming units (P.F.U.) adsorbed per flask. The excess virus was removed by washing four times with Earle's saline. The flasks of PII gourp were then refed with medium containning 50 μg/ml of PII and the flasks of control group were refed with medium only. The flasks of both groups were then incubated 24 hours at 37° C. The antiviral activity of the PII was determined as the reduction factor of viral titer from which $-\log_{10}TCD_{50}/ml$ was calculated.

TABLE 2

| | Number of sample | $-\log_{10}$ $TCD_{50}/ml$ | P (Treatment/ control) |
|---|---|---|---|
| Control | 30 | 5.7 | — |
| Rhabdoviridae | 30 | 2.0 | <0.1 |
| Reoviridae | 30 | 2.3 | <0.1 |
| Picornaviridae | 30 | 1.9 | <0.1 |
| Paramyxoviridae | 30 | 2.2 | <0.1 |
| Adenoviridae | 30 | 1.8 | <0.01 |
| Herpesviridae | 30 | 2.2 | <0.1 |

EXAMPLE 8

In vivo antiviral activity

PII was examined for its antiviral activity by lethal infection of mice with sendai virus.

A. Preparation of sendai virus:

1. Infected allantoic fluid containing 8000 hemagglutinating units (HAU) per ml is diluted to $10^{-4}$ with following solution:

| NaCl | 8.0 g |
|---|---|
| KCl | 0.3 g |
| $Na_2HP_4$ | 0.73 g |
| $KH_2PO_4$ | 0.20 g |
| glucose | 2.0 g |
| $H_2O$ | 1000 ml |

2. One tenth of a milliliter is injected into 9-day-old embryonated checken eggs certified as pathogen-free. The eggs are incubated at 36° C. in a humidified atmosphere for 72 hours.

3. After the incubation period, the eggs are placed at 4° C. for a minimum of 2 hours.

4. The allantoic fluid is harvested, pooled, and centrifuged at 400× g for 10 minutes at 4° C. The HAU titer of the supernatant fluid is determined.

5. The allatoic fluid is centrifuged at 2000× g for 20 minutes at 4° C. The supernatant fluid is decanted and saved, and the pellet is discarded.

6. The supernatant fluid is centrifuged at 16,000× g for 1 hour at 4° C. to pellet the virus.

7. After removing and discarding the supernatant fluid, the pellet is resuspended in 1 percent bovine serum albumin (BSA) in Hank's balanced salt solution without glucose to one tenth the volume of the original allantoic fluid. The virus can be dispersed by expelling the suspension through a needle attached to a syringe. This operation can be carried out in a stoppered serum bottle to avoid contamination of the environment.

8. The suspension is centrifuged at 2000× g for 20 minutes at 4° C. The supernatant fluid containg the virus is again tested to determine the HAU titer. The concentrated virus is stored in 1 ml lots at dry ice.

B. The mice were inrected with sendai virus and then PII was daily injected intraperitoneally. The mice were allowed to survive until 14 days. The dead animals were removed when discovered during the daily checks of the cages. The number of dead animals were recorded. The survival rate of PII and control groups was caculated. The following table shows that PII significantly increased that survival rate.

TABLE 3

| | Control | PII |
|---|---|---|
| Survival rate × 100% | 19.8 ± 1.5 | 85.9 ± 6.0 |
| Number of sample | 20 | 20 |
| P | | <0.1 |

EXAMPLE 9

The effect of PII on the DNA synthesis of virus-infected cells

The cell system consiste of monolayers of a continuous human cell line, the HEP cell, infected with herpes simplex virus (HSV). Approximately $10^6$ HEP cells in monolayer culture were washed with PBS solution. (8.0 g of NaCl, 0.3 g of KCl, 0.73 g of $Na_2HPO_4$, 0.2 g of $KH_2PO_4$, and 2.0 g of glucose to 1000 ml with $H_2O$). Then cells were washed with solution of virus. After infection the flasks were incubated for 20 minutes in a 37° C. At time the cells washed with PBS+0.4 ml of human γ-globulin. Scraped off, separated from each other by vigorous pipetting and, after 2 cycles of centrifugation, suspended in sufficient solution to yield approximately $3 \times 10^4$ cells per milliliter. Cell suspension (5–10 ml) was added to flasks equipped with a gas-tight glass cap. Flask were incubated at 34° C. Then flasks were thoroughly flush with air containing 5% $CO_1$. PII was added directly to the flasks of PII group. Same volume of physiological salt solution was added directly to the flasks of control group. To withdraw the PII solution or physiological salt solution. The cells were sedimented by centrifugation and resuspended in fresh MM-S solution.

MM-S: maintenance medium for suspended cells contains 7.17 g NaCl, 0.40 g KCl, 0.20 g $MgSO_4\ 7H_2O$, 0.125 g $NaH_1PO_4\ H_2O$, 0.20 g $CaCl_2$, 4.72 g of tryptose phosphate broth powder, 3.0 g glucose, 0.70 g $NaHCO_3$, 0.60 g glutamine, 20 mg of streptomycin sulfate, $2 \times 10^4$ unites of penicillin G, and water to make 1.3 liters. $^3$H-TdR was added to MM-S solution. The contents of each flask were divided into several replicate samples. Each sample received an equal volume of Saline-Citrate solution (SCS). The cells were then sedimented by centrifugation, washed twice in SCS, then resuspended in a solution of sodium lauryl sulfate (3%) in SCS. After 30 minutes at 37° C., an equal volume of 0.5N perchlorie acid (PCA) was added at room temperature. The precipitate was sedimented, washed twice with cold PCA, and finally, with ethanol. The precipitates were dissolved in 10× hyamine and added to scintillation counting mixture. The precipitate obtained with ethanol was redissolved in SCS and mixed with a solution of CsCl of known density. The mixture was then centrifuged. At that time even-numbered drops were collected in vials containing methanol. These received in addition hyamine and scintillation counting fluid. The counts of plulse of per minute (CPM) were determined by liquid scintillation counter.

TABLE 4

|  | Control | PII |
|---|---|---|
| CPM | 27918 ± 2899 | 8096 ± 791 |
| Number of sample | 20 | 20 |
| P | — | <0.01 |

It is clear that PII reduced by 70% the incorporation of $^3$H-TdR. These data shows that PII inhibited strongly DNA synthesis of virus-infected cells.

EXAMPLE 10

The effect of PII on lymphoblastoid transformation

The male mice weight 18-20 g were used in the experiments. The dosage of PII is 5.5 mg/kg injected intraperitoneally. The normal mice were injected with same volume of normal saline. These injections were repeated daily for 3-5 days. On the last day, both immunosuppressed and immunosuppressed+PII group immunosuppressive agents were injected interaperitoneally. Immunosuppressive agents include cortisone, cyclosporin A, prednisone, azathioprine, mercaptopurine, vincristine or chlorambucil. The experimental procedure of all examples in mice is similar to the above procedure.

(1) Lymphoblastoid transformation test:
I. Reagents and conditions for cell culture
  a. Culture media—RPMI 1640, madium 199 minimal essential medium (Eagle).
  b. 37° C. to maintain the pH of the medium at 7.3.
  c. Serum—generally 15-20% fetal bovine serum was incorporated, for lymphocytes from mice, 5% was used.
  d. Gaseous phase 5% $CO_2$ in air.
  e. Cell concentration—generally 1-2×10$^6$/ml.
  f. Stimulants: 20 μl/ml for phytoagglutinin containing polysaccharide (PHA-M) or 10 μl/ml for polysaccharide-free purified phytoagglutinin (PHA-P).
II. Measured by liquid scintillation
  a. The conditions of cell culture are same as above. $^3$H-TdR was added after 48 hours of incubation at a final concentration of 2 μCi/ml and continue the incubation for 24 hours.
  b. Wash the cells twice with cold normal saline and the erythrocytes were lysed by addition of distilled-water and equal volume of 3.6% NaCl was then added. The intact lymphocytes were again washed once with cold saline. Spin down the lymphocytes and add 2 ml of 10% trichloroacetic acid to precipitate the protein. Wash twice with normal saline. Add 2 ml of formic acid was then added for digestion till the precipitate was dissolved.
  c. Add 4 ml of scintillation fluid to 0.1 ml of the final sample and count in a liquid scintillation counter.
(2) Results are listed in the following tables:

TABLE 5A

|  | Normal | Immuno-suppressed | Immuno-suppressed + PII |
|---|---|---|---|
| CPM | 1340 ± 51 | 620 ± 58 | 1171 ± 50 |
| Number of sample | 10 | 10 | 10 |
| P | — |  | <0.01 |

*CPA: count of per minutes

TABLE 5B

|  | Normal | Immuno-suppressed | Immuno-suppresses + PII |
|---|---|---|---|
| Index of stimulation | 27.00 ± 3.20 | 13.12 ± 2.00 | 23 ± 2.2 |
| Number of sample | 12 | 12 | 12 |
| P | — |  | <0.1 |

EXAMPLE 11

The influence of PII on formation of resette

I. Method
  1. Obtain venous blood in heparin (10 IU ml$^{-1}$) and perform a tatal and differential leucocyte count.
  2. Isolate lymphocyte fraction. Count vaiable lymphocytes calculate and record total yield. Adjust to 5×10$^6$ lymphocytes ml$^{-1}$.
  3. Wash sheep erythrocytes by centrifugation (400 g for 10 minutes at room temperature) and adjust to a 2.5% v/v suspension in PBS.
  4. Mix 0.1 ml of the lymphocyte suspension with 0.1 ml of sheep erythrocytes and centrifuge at 225 g for 5 minutes at room temperature.
  5. Incubate for 2 hours at 4° C.
  6. Add 50 μl of fetal bovine serum (FBS) and 50 μl of nigrosin solution.
  7. Resuspend cell mixture by gently tapping the tube and pipette a sample into a haemocytomer.
  8. Count 200 lymphocytes and determine the percentage of cells with 3 or more erythrocytes attached. (These are T lymphocytes).
  9. Calculate the absolute number of T lymphocytes ml$^{-1}$ of original blood.
II. Results are listed following table:

TABLE 6

|  | Normal (%) | Immuno-suppressed | Immuno-suppressed + PII |
|---|---|---|---|
| Rate of formed rosette | 43.8 ± 2.0 | 20.7 ± 1.8 | 38.6 ± 3.4 |
| Number of sample | 12 | 12 | 12 |
| P | — |  | <0.01 |

EXAMPLE 12

The effect of PII on phagocytosis of peritoneal macrophage of mice

Add 0.02 ml of 5% washed chick red blood cell suspension to 0.5 ml of the peritoneal exudate, shake gently to mix and incubate at 37° C. for 5 minutes. Dip two coverslips, close to each other, in the above mixture and incubate for 30 minutes for the migration of the macrophages along the cover slips, fix and stain with sharma stain. Examine microscopically for:
  Phagocytic rate—number of macrophages with phagocytized chick red blood cells per 100 macrophages counted.

Results: The results as illustrated by the following table:

TABLE 7A

| Phagocytic percent + SD(%) | Normal | Immuno-suppressed | Immuno-suppressed + PII |
|---|---|---|---|
| Number of sample | 35.10 ± 2.01 | 19.8 ± 1.8 | 29.9 ± 2.6 |
| P | — | | <0.01 |

$^{53}$Cr lablling method:

Method—Count the number of macrophages in the peritoneal exudate of mice and adjust to $1 \times 10^7$ cell/ml with normal saline. Add 0.1 ml of the macrophage suspension. i.e. $1 \times 10^6$ cells to each well on the plastic plate for test. Lable the chick red blood cell with $^{53}$Cr. Suspend the labelled chick red blood cell and adjust to $1.5 \times 10^8$/ml, add 0.1 ml, i.e. $1.5 \times 10^7$, to each well. Incubate at 37° C. for 30 minutes. Wash thoroughly to remove the free chick red blood cells. Count each well in a $\gamma$-counter.

The results are listed bellow table.

TABLE 7B

| | Normal | Immuno-suppressed | Immuno-suppressed + PII |
|---|---|---|---|
| CPM | 1089 ± 341 | 481 ± 44 | 835 ± 70 |
| Number of sample | 12 | 12 | 12 |
| P | — | | <0.1 |

EXAMPLE 13

The influence of PII on particle clearance by the reticuloendothelial system

Method:
(1) Warm the mouse at 37° C. for 15–20 minutes.
(2) Snip the end from the tail and collect one drop of blood onto a microscope slide. Lyse a 20 µl sample in 4.0 ml of acetic acid.
(3) Inject 0.1 ml of colloidal carbon into the tail vein. (Inject near to base of tail.)
(4) When the mouse's eyes have turned black (within 30 sec.) collect one drop of blood and lyse a 10 µl sample in 2 ml of acetic acid.
(5) Collect one drop of blood at the following times postinjection: 2, 5, 10, 15, 20, 30, 45, 60 and 90 minutes and lyse a 10 µl sample, before it clots, in 2 ml of acetic acid solution.
(6) Observe the colour change of the mouse's eyes. Kill the mouse and examine.
(7) Using the original pre-injection blood sample as a standard read the density of all the lysed samples.
(by stuara A E. et al phagocytes in vitro in "handbook of Experimental immunology" Vol. 2 Cellular Immunology p: 23. 31. Thira-ed weir DM Blackur oxford. 1978. London).

TABLE 8

| | Normal | Immuno-suppressed | Immuno-suppressed + PII |
|---|---|---|---|
| Particle clearance | 4.53 ± 0.03 | 2.08 ± 0.2 | 3.72 ± 0.1 |
| Number of sample | 18 | 18 | 18 |

TABLE 8-continued

| | Normal | Immuno-suppressed | Immuno-suppressed + PII |
|---|---|---|---|
| P | — | | <0.1 |

EXAMPLE 14

The effects of PII on immune function of human blood lymphocytes 20 old volunteers (60–70 years of age) participated in the the experement.

2 ml of venous blood, heparinized was obtained. The study of the effects of PII was carried out by using Eagle's Minimal Essential Medium (MEM). MEM was supplemented with 0.12 ml of heat-inactivated fetal calf serum, 100 units of Penicillin and 0.1 mg of streptomycin per ml of medium. Culture medium was divided into treated (PII) and control group. PII was added to the culture medium of PII group (a final ethanol concentration is 150 µg/ml) on the 72 hours of culture. The culture medium of control group was added with same volume of normal saline on the 72 hours of culture. The $^3$H-thymidine ($^3$H-TdR) was added into cultures (2 µci/ml) for last 12 hours of culture. The cells were harvested on 0.45 µm millipore filters, washed with phosphate buffer (pH 7.4) and bleached with $H_2O_2$. The filters were then dried and the incorporation of $^3$H-TdR into lymphocytes cell was measured by scintillation counter.

TABLE 9

| | Old (n = 20) | |
|---|---|---|
| | control | PII |
| CPM/10 cells | 22498 ± 1895 | 29247 ± 1809 |
| T/C | | 130.0% |
| P | | <0.01 |

According Table 9, PII was found to increase lymphoblastoid transformation of old person.

EXAMPLE 15

Safeness of PII

1. L.D$_{50}$: 1179 mg/kg injection in abodominal cavity in mice.
2. Each dose for a n adult is 5–10 mg. Using 50 kg as the average weight of an adult the dosage is 1–2 mg/kg, therefore it is very safe.

The preparation of PII is simple and can be accomplished by the extraction methods set forth above or any conventional methods for extracting the active ingredients from the plant tissues. The novelty of the present invention resides in the mixture of the active ingredients in the specified proportions to produce PII and in the preparation of dosage units in pharmaceutically acceptable dosage form. The term "pharmaceutically acceptable dosage form" as used hereinabove includes any suitable vehicle for the administration of medications known in the pharmacseutical art, including, by way of example, tablets, capsules, syrups, elixirs, and solutions for parenteral injection with specified ranges of PII concentration. The present invention provides novel methods for inhibiting viruses and increasing immunofunction with easily produced, safe pharmaceutical agent.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

I claim:

1. A process for producing Banlankensu from powdered roots of a plant selected from the group consisting of *Isatis tinctoria* L, *I. indigotica* Fort and *Baphicacanthus cusia* Bremek comprising:

(a) extracting said powder with 95% ethanol at room temperature for 24 hrs;

(b) separating the extract from the powder;

(c) refluxing the separated powder of step (b) twice with ethanol over a water bath for 6 hours, separating the ethanol extracts from the powder, and combining all the extracts;

(d) distilling the extract under reduced pressure to yield a residue;

(e) dissolving the residue in water;

(f) extracting the resulting solution with ether and recovering the aqueous layer;

(g) extracting the aqueous layer with an equal volume of water-saturated butanol;

(h) distilling the water-butanol layer to yield a residue;

(i) dissolving the residue in ethanol;

(k) precitating the Banlankensu with acetone, washing the precipitate twice with acetone and twice with ether; and (l) drying the Banlankensu.

* * * * *

UNITED STATES PATENT AND TRADEMARK OFFICE
CERTIFICATE OF CORRECTION

PATENT NO. : 4,944,945
DATED : July 31, 1990
INVENTOR(S) : Yaguang Liu

It is certified that error appears in the above-identified patent and that said Letters Patent is hereby corrected as shown below:

Title page, item [76] Inventor: change "Yaguang Lui" to read --Yaguang Liu--.

Signed and Sealed this

Seventeenth Day of November, 1992

Attest:

DOUGLAS B. COMER

Attesting Officer       Acting Commissioner of Patents and Trademarks